(12) United States Patent
Park et al.

(10) Patent No.: US 7,027,640 B2
(45) Date of Patent: Apr. 11, 2006

(54) METHOD AND APPARATUS FOR INSPECTING DEFECTS ON POLISHING PADS TO BE USED WITH CHEMICAL MECHANICAL POLISHING APPARATUS

(75) Inventors: Sung-Jin Park, Pyungtaek (KR); Chan-Ho Ryu, Anyang (KR)

(73) Assignee: Nanometrics Incorporated, Milpitas, CA (US)

( * ) Notice: Subject to any disclaimer, the term of this patent is extended or adjusted under 35 U.S.C. 154(b) by 757 days.

(21) Appl. No.: 10/226,850

(22) Filed: Aug. 23, 2002

(65) Prior Publication Data

US 2003/0039387 A1 Feb. 27, 2003

(30) Foreign Application Priority Data

Aug. 27, 2001 (KR) ................. 2001-51891

(51) Int. Cl.
*G06K 9/00* (2006.01)

(52) U.S. Cl. .............. 382/152; 382/149; 382/312; 250/559.14; 356/237.1; 356/237.2

(58) Field of Classification Search ............. 382/149, 382/145, 152, 312; 356/237.1, 237.2, 237.3–6, 356/394, 503; 451/5–8, 41, 285; 438/690–693
See application file for complete search history.

(56) References Cited

U.S. PATENT DOCUMENTS

| 6,201,253 | B1 * | 3/2001 | Allman et al. ......... 250/559.27 |
| 6,315,634 | B1 * | 11/2001 | Jensen et al. .................. 451/5 |
| 6,431,959 | B1 * | 8/2002 | Mikhaylich et al. .......... 451/41 |
| 6,608,921 | B1 * | 8/2003 | Inoue et al. ................. 382/146 |
| 6,650,408 | B1 * | 11/2003 | Jun et al. .................. 356/237.2 |
| 6,705,930 | B1 * | 3/2004 | Boyd et al. .................. 451/286 |
| 2002/0063860 | A1 | 5/2002 | Jun et al. ................. 356/237.2 |

FOREIGN PATENT DOCUMENTS

| JP | 10-086056 | 7/1998 |
| JP | 11-277405 | 12/1999 |

* cited by examiner

*Primary Examiner*—Sheela Chawan
(74) *Attorney, Agent, or Firm*—Silicon Valley Patent Group LLP (57) ABSTRACT

The present invention provides an apparatus and method for detecting or inspecting defects on a polishing pad for use in performing chemical mechanical polishing of a wafer. The apparatus for detecting the defects on the pad comprises a pad driving device for loading the pad thereon and moving the pad, at least one camera installed to face the pad for converting an image of the pad into an electrical signal and outputting the converted electrical signal, a digital image data acquisition device for converting the electrical signal transmitted from the camera into a digital signal, and an image data processing unit for processing the image data and detecting the defects on the pad.

20 Claims, 8 Drawing Sheets

METHOD AND APPARATUS FOR INSPECTING DEFECTS ON POLISHING PADS TO BE USED WITH CHEMICAL MECHANICAL POLISHING APPARATUS

CROSS REFERENCE TO PRIOR APPLICATION

This application claims priority to a Korean Patent Application having application number 01-51891, filed Aug. 27, 2001, entitled "Method And Apparatus For Inspecting Defects On Polishing Pad To Be Used With Chemical Mechanical Polishing Apparatus".

BACKGROUND OF THE INVENTION

1. Field of the Invention

The present invention relates to a method and apparatus for inspecting defects on a polishing pad to be used with a polishing apparatus for performing chemical mechanical polishing of a wafer.

2. Description of the Prior Art

In a semiconductor manufacturing process, surfaces of wafers coated with predetermined thin films may not be frequently flat. If surfaces are not uniformly even, an accurate circuit pattern cannot be obtained from the next photolithographic process. In order to avoid such a problem, the surface which is not flat should be polished. That is, the wafer is spun or rotated in a state where it is pushed toward a polishing pad while spraying slurry, i.e. a suspension which includes inorganic particles and surfactants, onto the polishing pad. Then, the wafer surface can be polished to be flat through the combination of mechanical friction between the wafer and suspension and chemical dissolution reaction of the suspension. This process is called chemical mechanical polishing (CMP).

Recently, since a critical dimension of the semiconductor has rapidly decreased, a process tolerance which is permitted in the photolithographic process has also rapidly reduced. Thus, the need for chemical mechanical polishing has remarkably increased. Most domestic and foreign semiconductor factories have introduced several dozens of the polishing apparatus per factory while introducing this process.

One of the problems of the process is that a surface scratch occurs during the polishing process. In a case where a surface of the wafer is severely scratched, the wafer may be discarded due to potential damage to a circuit to be printed on the wafer. That's because even a fine scratch will deteriorate efficiency of the next photolithographic process, thereby reducing throughput yield.

There are several reasons why such scratches are generated. First, a scratch may result when excessively large inorganic particles are included in the slurry. Further, the scratch may be produced when the particles in the slurry are agglomerated during the polishing process. Furthermore, the scratch may be produced when any external particles are dropped onto the pad. For example, any metallic fragments may drop from mechanical parts of the polishing apparatus. In addition, diamond particles produced during diamond pad conditioning, performed to improve an operating condition of the pad used for a specific period of time, may cause a scratch. Moreover, if any particles are dropped on the polishing pad before the polishing operation or any particles included in the polishing pad protrude from a surface of the pad when the pad intends to be used, problems are caused.

The problems occurring from the slurry have been greatly solved by inspecting the slurry using various measuring equipment and by filtering out unnecessary particles using some filters. The problems resulting from a diamond pad conditioner have also been almost solved through endeavors to improve quality of the conventional diamond pad conditioner. However, sufficient methods for the inspection or processing of the defects on the polishing pad itself have not yet been achieved.

SUMMARY OF THE INVENTION

In order to solve the above problems in the prior art, the present invention provides a method and apparatus for inspecting defects on a polishing pad for use in chemical mechanical polishing of a wafer. Accordingly, the wafer can be protected by inspecting the defects on the polishing pad.

Further, the present invention provides an apparatus for preventing any defective pads from being used in the apparatus by detecting any particles, which originally have adhered to or been included in the pad, or other defects of the pad, and for detecting defects, which cause the wafer to be scratched, by inspecting a relevant pad when a wafer scratch phenomenon occurs. A method of detecting defects through image data processing according to the present invention is basically used to analyze whether values such as gray scales of respective pixels on an image of the pad are greatly different from those of surrounding pixels.

According to the present invention, there are advantages in that a poor process due to pad defects can be beforehand avoided by removing the pad defects, and guidelines on improving the process in the future can be obtained by finding out causes of the defects already generated. Further, easy understanding of correlation between the process and the defects and between the yield and the defects can be made based on a short-term or long-term trend of the polishing pad obtained by categorizing images of detected defects according to sizes and types thereof and statistically processing the images of the defects after detecting defects on the pad.

According to an aspect of the present invention, there is provided an apparatus for detecting or inspecting defects on a pad for use in performing chemical mechanical polishing of a wafer, which comprises a pad driving device for loading the pad thereon and moving the pad, a camera installed to face the pad for converting an image of the pad into an electrical signal and outputting the converted electrical signal, a digital image data acquisition device for converting the electrical signal transmitted from the camera into a digital signal, and an image data processing unit for processing the image data and detecting the defects on the pad.

In a preferred embodiment of the present invention, the camera is a linescan camera including a monochrome or color line CCD extending in a radial direction of the pad. Further, the pad driving device includes a turntable for causing the pad to rotate about the substantial center thereof. In particular, the line CCD of the linescan camera is disposed such that a longitudinal direction thereof is coincident with the radial direction of the pad.

The apparatus for detecting the defects on a pad further comprises an illuminating device facing a surface of the pad. The illuminating device includes a supporting body in which a slit extending in the radial direction of the pad is included, and a light emitting device which extends along the slit and is installed around the slit to face the pad.

In the image data processing unit, one or more of quantitative characteristic values of light based on the image data on any one of points which are acquired from the image data acquisition device is calculated. Then, a location on the pad, where a difference between a level value obtained by combining one or more of the acquired quantitative characteristic values and a level value obtained from a normal surface of the pad is greater than a predetermined value, is determined as a defect. Further, the image data processing unit is constructed such that it calculates an average of the level values of points adjacent to the specific point and subtracts the average level value from the level value of the specific point when processing data on any one specific point on the pad, thereby eliminating the effects of the grooves and the like.

The pad driving device includes a turntable for causing the pad to rotate about the substantial center thereof, and synchronized a pulse signal corresponding to a predetermined angle of rotation of the turntable with a trigger signal of the image data acquisition device.

According to another aspect of the present invention, there is provided a method for detecting or inspecting defects on a polishing pad for use in performing chemical mechanical polishing of a wafer, which comprises the steps of rotating the polishing pad about the center thereof, acquiring an image of a top surface of the polishing pad along a line extending in a radial direction thereof, converting the image into an electrical signal, converting the electrical signal into digital image data, and processing the digital image data.

According to a further aspect of the present invention, there is provided a computer-readable recording medium into which a program executed by a processor for processing image data is recorded. The program causes the processor to execute the steps of calculating one or more of quantitative characteristic values of light based on the image data on any one of points which are acquired from the image data acquisition device, and calculating a difference between a level value obtained by combining one or more of the acquired quantitative characteristic values and a level value obtained from a normal surface of the pad, and confirming whether or not the difference is greater than a predetermined value.

BRIEF DESCRIPTION OF THE DRAWINGS

The above and other objects, features, and advantages of the present invention will become more apparent when reading the following description of preferred embodiments of the present invention given in conjunction with the accompanying drawings, in which.

DETAILED DESCRIPTION OF THE INVENTION

Hereinafter, a method and apparatus of the present invention will be explained in detail with reference to the accompanying drawings.

Figure 1:
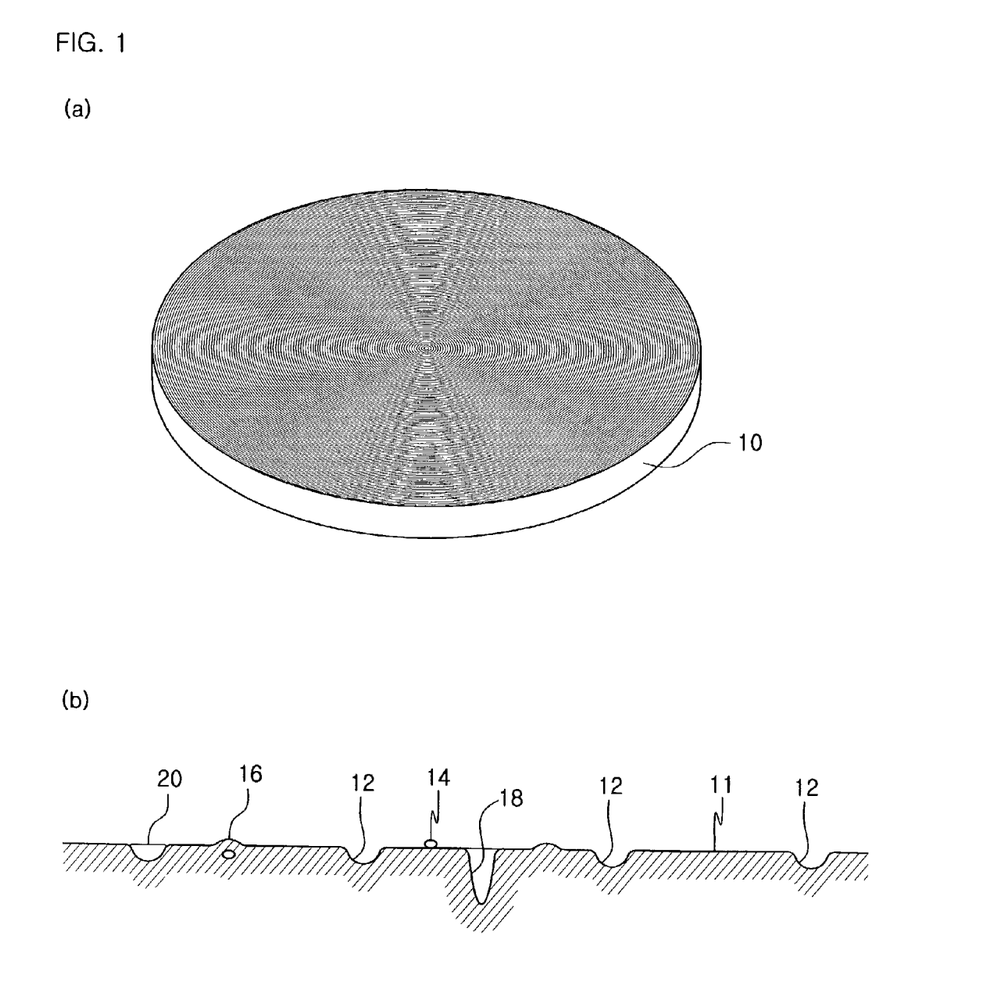
FIG. 1(a) is a perspective view of a polishing pad.
FIG. 1(b) is a partial sectional view of a surface of the polishing pad.

FIG. 1 shows a polishing pad 10. Referring to FIG. 1(a), the polishing pad 10 is in the form of a disk. A diameter of the polishing pad is about 50 cm, but the present invention is not limited thereto. For example, the polishing pad 10 is made of resin material such as polyurethane. Referring to FIGS. 1(a) and (b), a plurality of concentric grooves 12 are formed on a surface 11 of the polishing pad from the center to the edge of the polishing pad. The grooves 12 are used for inflow and outflow of slurry. The grooves are hollowed in the form of concentric circles from the center to the edge of the polishing pad. Although they are not specifically illustrated in the figure, extremely fine small holes, which are called pores, are also formed on the surface of the polishing pad, like a sponge. These pores are used to improve polishing performance.

Referring again to FIG. 1(b), there are shown various types of defects on the surface 11 of the polishing pad 10. (Although the term 'defect' is generally used to indicate intrinsic defects which can be differentiated from particles, it is explained herein that the particles are also included within a category of the defect.) For example, the defects include particles 14, spots 16, red spots, holes 18, bridges 20, and the like. These defects can be automatically classified on the basis of characteristics of colors and shapes thereof. The respective defects have their own inherent characteristics of colors and shapes. The characteristics of colors can be detected by finding out the characteristics of colors different from that of a color of the normal surface of the pad through comparison therebetween. The characteristics of shapes can be detected by finding out the characteristics of sizes, outer appearance and the like of the defects. Types of defects are determined by synthesizing the characteristics which have been weighted according to the respective characteristics. Hereinafter, the respective defects will be explained in detail.

1. Particles

The particles 14 corresponding to one of the defects are foreign materials which are dropped onto the surface 11 of the polishing pad 10 from the outside. The particles have remarkably dark colors (black) as compared with the normal surface 11 of the pad. Further, color transitions between the particles and the normal surface 11 of the pad are sharp. The particles have relatively small sizes of about 50 to 200 μm. The particles have the following characteristics:

HSI model analysis

Since the particles are black, their values of intensity or luminous intensity (sometimes referred to as luminosity) are rapidly lowered.

RGB model analysis

While the normal surface of the pad is pale yellow, the particles are black. A pale yellow color has such a value that a red level (often referred to as an R level) is high, a green level (often referred to as a G level) is slightly lower than the red level, and a blue level (often referred to as a B level) is relatively low. On the other hand, a black color has such a value that all the R, G and B levels are close to zero. Thus, an R level difference between the normal pad surface and the particles is most high, a G level difference therebetween is slightly high, and a B level difference therebetween is not higher than the R and G level differences.

A basic method of determining any defects on the pad as the particles is as follows. That is, an average intensity value $I_{pad}$ of the pad surface and an average intensity value $I_{defect}$ of the defects are first obtained. Then, if a difference between the values $I_{pad}$ and $I_{defect}$ is greater than a predetermined value A, the defects are determined as the particles.

2. Spots

The spots are the defects due to foreign materials included in the pad during the process of manufacturing the pad. The spots have colors which are similar to or relatively less dark than that of the normal pad surface. The color transitions between the normal pad surface and the spots are smooth. The spots have relatively large sizes of about 300 to 2,500 µm. The spots have the following characteristics.

HSI model analysis

Since a color difference between the spots and the normal pad surface is not great, hue (or tint) values of the spots are not much different from that of the normal pad surface. The intensity values of the spots are relatively lower than that of the normal pad surface. Further, the intensity transitions between the normal pad surface and the spots are smooth.

A basic method of determining any defects on the pad as the spots is as follows. That is, the defects are determined as the spots in a case where a difference between the values $I_{pad}$ and $I_{defect}$ is large enough to be considered as the defects but is equal to or lower than a predetermined value B, and a difference between average hue values $H_{pad}$ and $H_{defect}$ of the normal pad surface and the defects is large enough to be considered as the defects but is equal to or lower than another predetermined value.

3. Red Spots

The red spots are relatively reddish defects among the defects due to foreign materials included in the pad during the process of manufacturing the pad. The red spots are not much different from the aforementioned general spots in view of their technical senses. However, the red spots are reddish, whereas the general spots are gray. Further, the red spots have a high frequency of occurrence among the spots. From the viewpoint of color, the red spots are similar to the normal pad surface and relatively reddish. The color transitions between the normal pad surface and the red spots are smooth. The red spots have relatively large sizes of about 300 to 2,500 µm and wide breadths. The red spots have the following characteristics.

HSI model analysis

The red spots have characteristics similar to those of the general spots. The hue values of the red spots are relatively close to that of the red color.

RGB model analysis

The red spots are the relatively reddish spots having such values that their R levels are higher than their G and B levels. When the red spots are compared with the normal pad surface, the R level of the red spots is higher than or similar to that of the normal pad surface. However, the G and B levels of the red spots are lower than those of the normal pad surface.

A basic method of determining any defects on the pad as the red spots is as follows. That is, the defects are determined as the red spots in a case where a difference between the values $I_{pad}$ and $I_{defect}$ is large enough to be considered as the defects but is equal to or lower than a predetermined value C, a difference between the average hue values $H_{pad}$ and $H_{defect}$ thereof is large enough to be considered as the defects but is equal to or lower than another predetermined value, and the hue values of the defects are close to that of the red color.

4. Holes

The holes are generally generated during the process of manufacturing the pads, and correspond to semicircular holes formed onto the surface of the normal pad. The color of the holes is the same as the pad surface, but only brightness thereof becomes darker. In particular, the brightness becomes darker from edges to the centers of the holes. The brightness of the holes is rapidly changed at the edges of the holes, but is hardly changed at the centers thereof. The holes have relatively large sizes of about 500 to 1,500 µm. The holes have the following characteristics.

HSI model analysis

The hue values of the holes are about the same as that of the normal surface of the pad, and the intensity values of pixels corresponding to the holes are slightly lowered uniformly all over the pad surface.

Thus, the pixels of which brightness is different from that of normal pad surface by a predetermined value are determined as the holes.

5. Bridges

The bridges are the defects due to blockage of the grooves on the pad during the process of manufacturing the pad. The bridges are made of the same material as the pad. The color of the bridges is somewhere between the colors of the pad surface and grooves. These defects are formed along the grooves. The characteristics of the bridges are as follows.

HSI model analysis

The hue values of the bridges are about the same as that of the normal pad surface, and the intensity values of pixels corresponding to the bridges are slightly lowered uniformly all over the pad surface.

The hue values of the bridges are between the hue values of the normal pad surface and the grooves. Thus, if such hue values are detected at positions of the grooves along a scanning direction (circumferential direction), it is determined that there are the bridge defects in the groove positions.

It is preferred that the following steps be performed when these defects are detected and determined according to the present invention. First, the defects are detected by analyzing data acquired from a monochrome linescan camera. That is, it is determined that when gray scale values obtained from monochrome image data of the defects have been compared with those of portions around the defects, there are some defects in locations where appreciable differences between the compared data are observed. If the kinds of defects are not still classified distinctively in the first step although they are determined as the defects in the first step, the defects are secondarily classified based on the color image data on the defects and the portions around the defects. The defects are discriminated and classified into the above kinds thereof based on the aforementioned characteristics thereof by using the HSI values and the like. If the determined defects are the general particles, they may be removed by using a method of blowing away the particles using compressed air. Further, in a case where it is difficult to remove the defects since they are the spots and the like which are generated during the process of manufacturing the pad, these result data on classification thereof are used as base data when it is necessary to return the polishing pads to the manufacturer.

Figure 2:
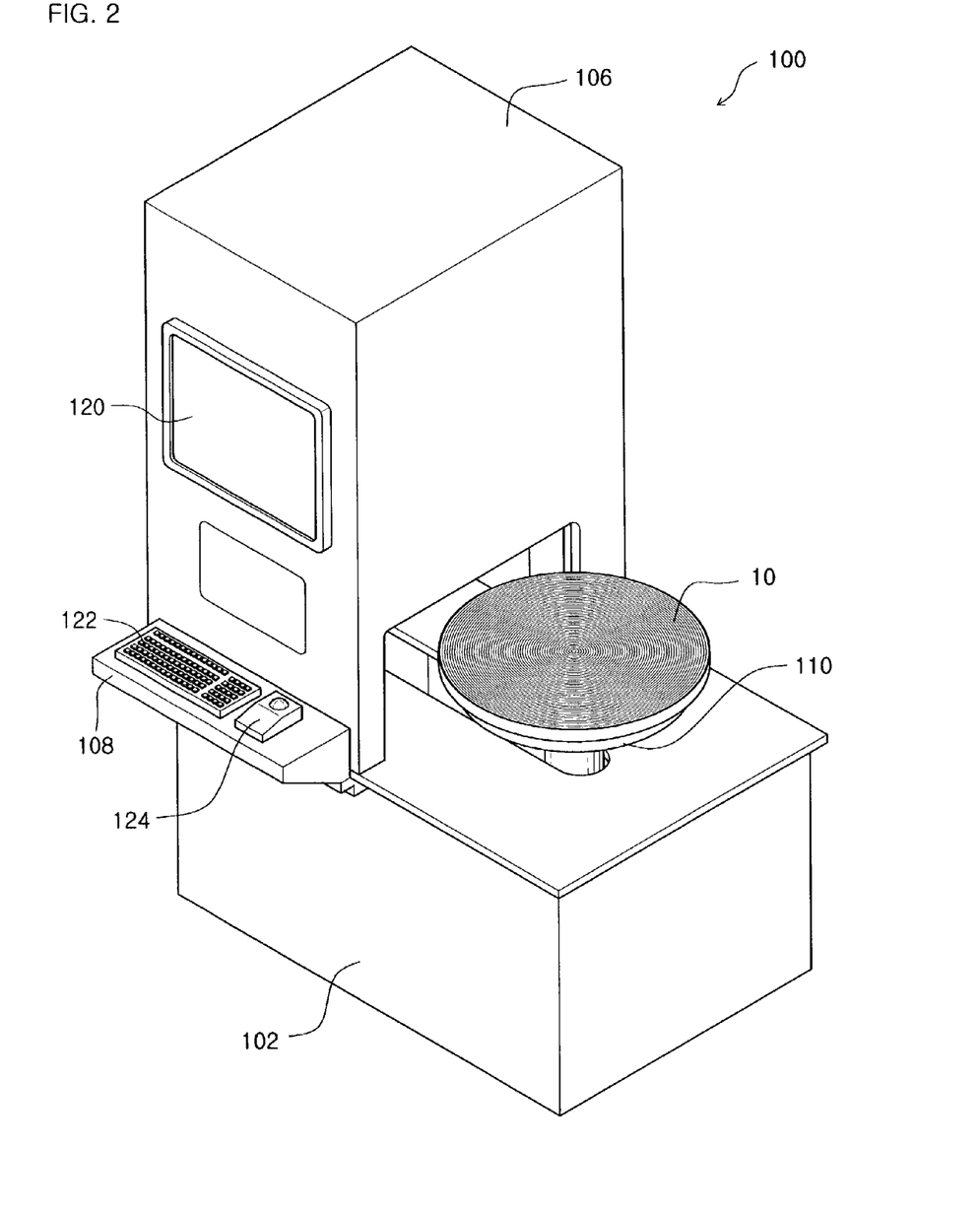
FIG. 2 is a perspective view of an apparatus for inspecting defects on the polishing pad according to an embodiment of the present invention.
Figure 3:
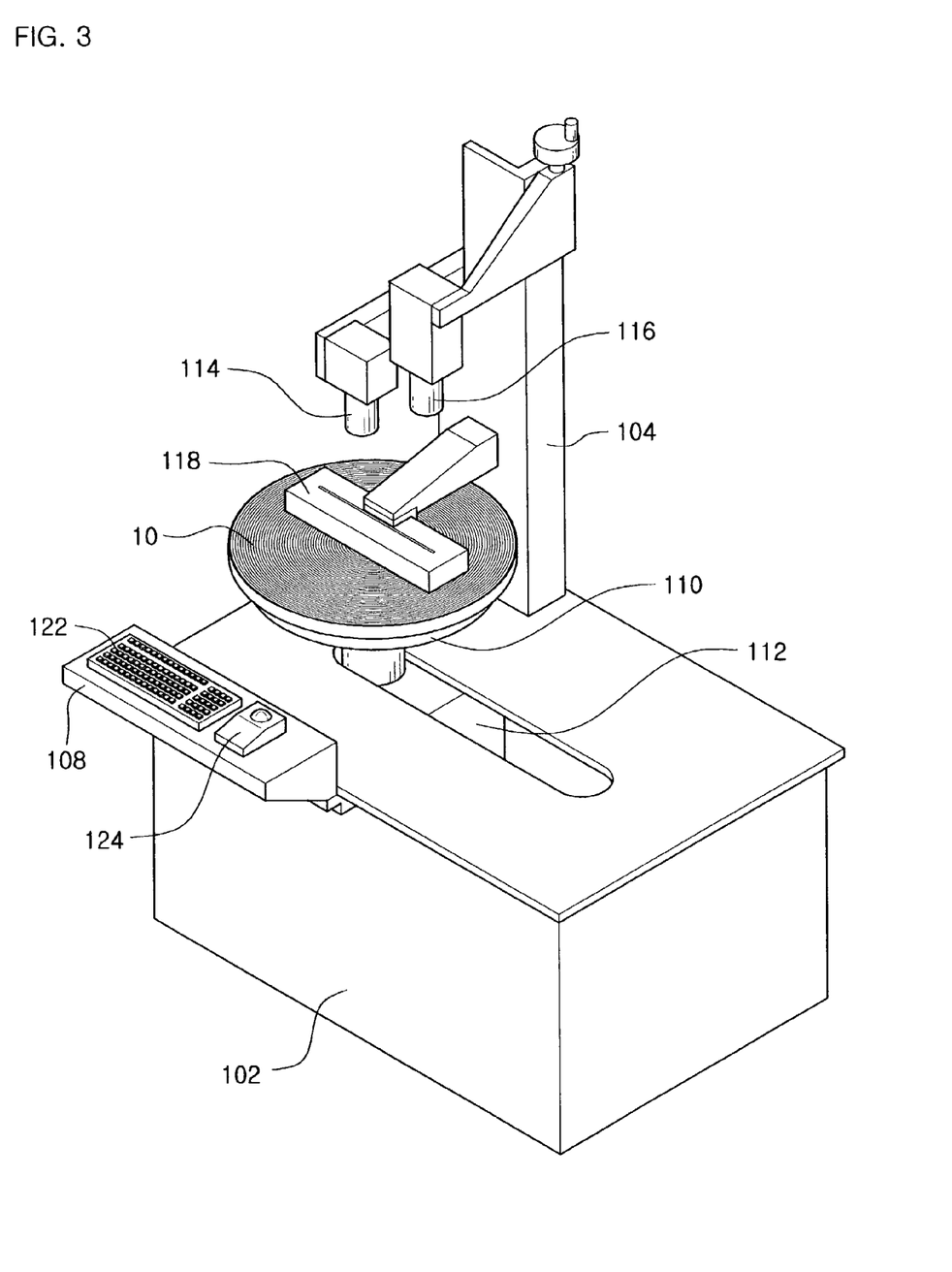
FIG. 3 is a perspective view of the apparatus of FIG. 2 wherein a case is removed so that the interior thereof can be easily shown.

Referring to FIGS. 2 and 3, an apparatus 100 for inspecting defects on the pad according to the present invention comprises a bed 102, a support 104 fixed onto the bed, a case 106 for covering some parts including the support 104, and a supporting shelf 108 installed on the front of the case 106. FIG. 3 shows the interior of the case 106 with the case 106 removed. Various kinds of circuit devices, a turntable 110 and a linear moving device 112 for linearly moving the turntable 110, which will be explained later, are installed onto the bed 102. The polishing pad 10 to be inspected is also loaded onto the turntable 110. The support 104 is installed vertically on a side of the bed. A monochrome linescan camera 114 and a color linescan camera 116, which face the pad located below the cameras, are installed to the support 104. Further, an illuminating device 118 is installed below the cameras 114, 116 to the support 104. A display device 120 is installed on the case 106. Input devices such as a keyboard 122 and a point input device 124 are positioned onto the supporting shelf 108.

Figure 4:
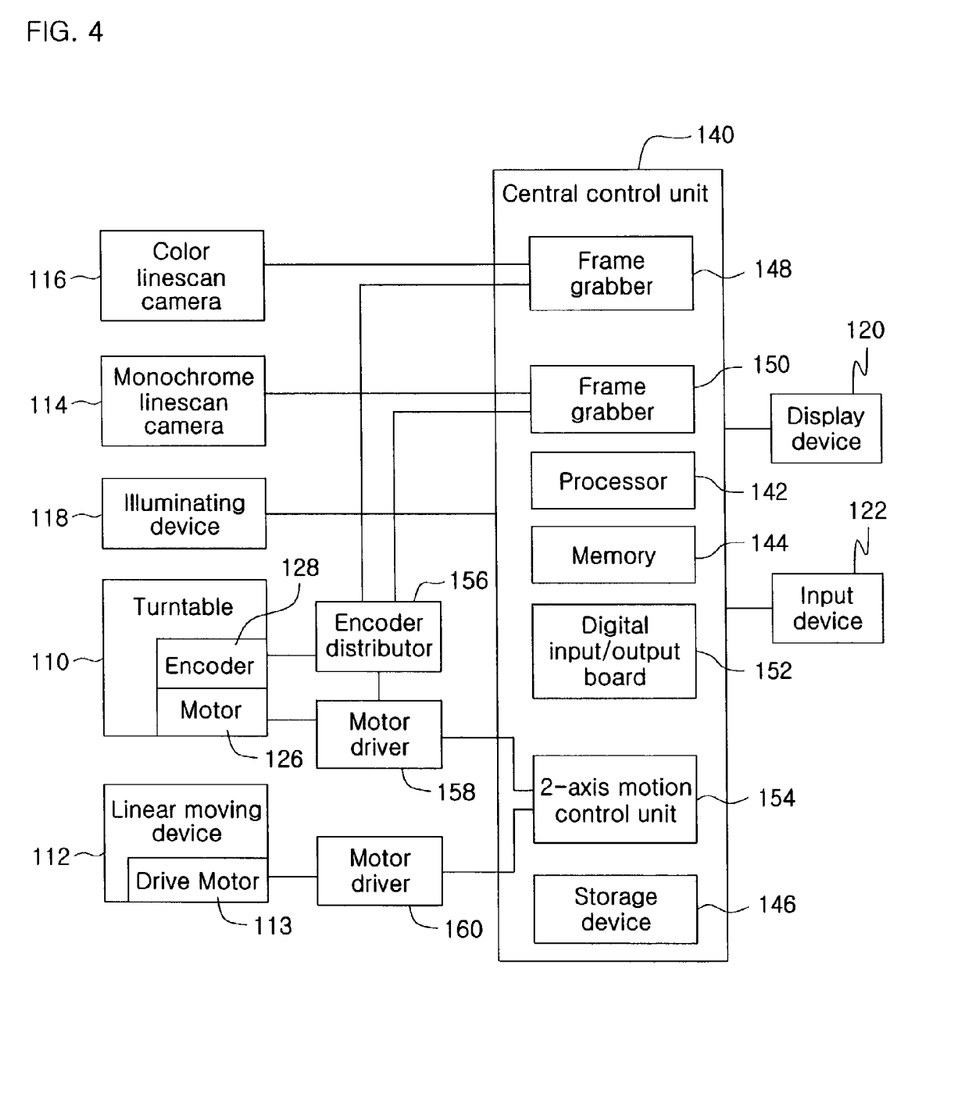
FIG. 4 is a view showing a system configuration of the apparatus for inspecting the defects on the polishing pad according to the embodiment of the present invention.

Referring to FIGS. 2 to 4, the turntable 110 is used to rotate the pad 10 loaded thereon. The turntable 110 is constructed such that the pad 10 can be installed thereon in a state where the center of the pad 10 coincides with the center of the turntable 110. By way of example, a vacuum attachment device is installed to the turntable 110 so as to perform vacuum attachment and install the pad thereon. The turntable 110 includes a rotary drive motor 126 and a rotary encoder 128. It is preferred that the drive motor 126 be a precise stepping motor. For example, the precise stepping motor is known as a micro stepping motor and is used to divide a fundamental step pulse into 125 pulses and to generate maximum 3,250,000 pulses per one revolution. Considering that a length of one step at an outermost edge of the pad is about 0.46 µm while a minimum size of one pixel captured by the camera of the apparatus is 15 µm, it can be understood that the stepping motor is able to perform a very precise control. For example, the precise stepping motor (Model No.: VEXTA Step PK599BW available from Oriental Motor Co., Ltd. in Tokyo, Japan) may be utilized for constructing the turntable 110 for precisely rotating the pad 10. A motor driver (Model No.: DFU1514W available from the same company) may be used for driving the precise stepping motor. Although it is not illustrated in detail, it is preferred that the turntable 110 be provided with a vacuum attachment fixture for fixedly holding the pad 10 onto the turntable 110.

Referring still to FIGS. 2 to 4, the linear moving device 112 causes the turntable 110 to move linearly between a loading position shown in FIG. 2 and an inspecting position shown in FIG. 3. Further, the linear moving device 112 can cause the turntable 110 to move by a predetermined pitch (a value lower than a radius of the pad) at the inspecting position. The linear moving device 112 may be a linear motor. In general, the linear moving device 112 may be composed of a rotary drive motor 113, which is a precise stepping motor, and a mechanism for converting a rotary motion into a linear motion.

Referring to FIGS. 3 and 4, the monochrome linescan camera 114 is installed to the support 104. The monochrome linescan camera 114 is installed to face the pad 10, i.e. to face vertically downward, when the pad 10 is located at the inspecting position. The monochrome linescan camera 114 includes a line CCD therein. The line CCD converts transmitted light into an electrical signal and transmits the signal to a control unit which will be described later. The line CCD is installed in the linescan camera such that a longitudinal direction thereof is coincident with a radial direction of the pad located at the inspecting position. Further, if a trajectory along which the center of the pad 10 moves is defined as a moving axis, the longitudinal direction of the line CCD is parallel to the moving axis when the linear moving device 112 causes the pad 10 to be shifted from the inspecting position by the predetermined pitch. The monochrome linescan camera (Model No.: Dalsa SP-12-02K40 available from DALSA, Inc. in Ontario, Canada, of which website is www.dalsa.com) is an example of such a monochrome linescan camera 114.

Referring to FIGS. 3 and 4, the color linescan camera 116 is installed to the support 104 beside the monochrome linescan camera 114. Similarly to the monochrome linescan camera 114, the color linescan camera 116 is also installed to face the pad 10, i.e. to face vertically downward, when the pad 10 is located at the inspecting position. The color linescan camera 116 includes a color line CCD therein. The color line CCD converts transmitted light into an electrical signal and transmits the signal to the control unit to be described later. Similarly to the monochrome linescan camera 114, the color linescan camera 116 is installed such that a longitudinal direction of the color line CCD is coincident with the radial direction of the pad located at the inspecting position. Further, the longitudinal direction of the line CCD is parallel to the moving axis of the pad when the linear moving device 112 causes the pad 10 to be shifted from the inspecting position by the predetermined pitch. In the embodiment of the present invention, both the longitudinal directions of the monochrome and color linescan cameras and the moving axis of the pad are positioned in one vertical plane. The color linescan camera (Model No.: JAI CV-L103 available from JAI Corporation in Yokohama, Japan) is an example of such a color linescan camera 116.

The monochrome and color linescan cameras 114, 116 are able to move vertically so that they can be brought into focus on the respective pads 10. However, if the pads 10 are standardized in practice, the monochrome and color linescan cameras 114, 116 may be fixed at a predetermined vertical position.

Figure 5:
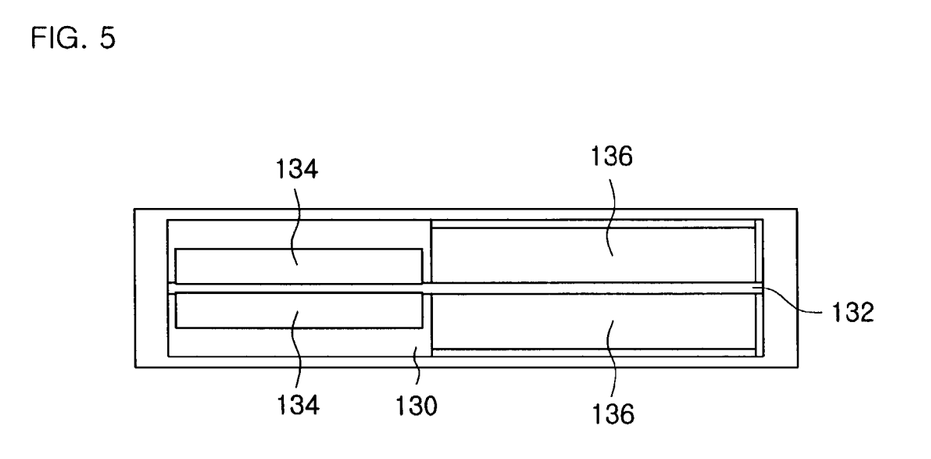
FIG. 5 is a bottom view of an illuminating device installed within the apparatus of FIG. 2.
Figure 6:
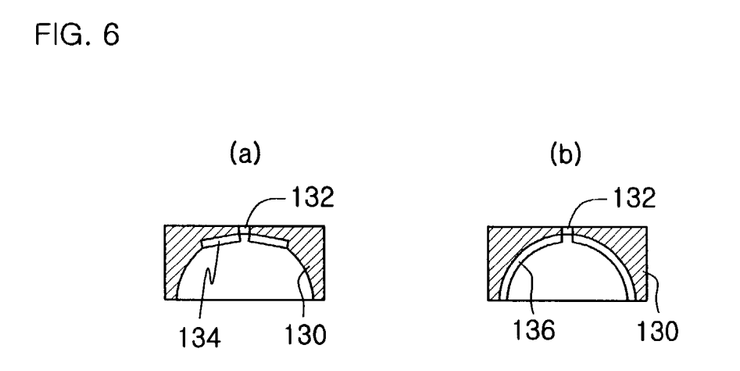
FIG. 6 is a longitudinal sectional view of the illuminating device of FIG. 5, wherein (a) is a longitudinal sectional view of a monochrome imaging illuminating unit of the illuminating apparatus, and (b) is a longitudinal sectional view of a color imaging illuminating unit of the illuminating apparatus.

Referring to FIGS. 3, 5 and 6, the illuminating device 118 is installed between the cameras 114, 116 and the pad 10, and particularly at a position adjacent to the pad 10. The illuminating device 118 is fixed to the support 104 and has a long length along the moving axis of the pad. The illuminating device 118 is constructed such that a round groove is formed to extend along the moving axis of the pad onto a bottom side of the illuminating device. An inner surface of the groove serves as a reflecting surface 130. It is preferred that the reflecting surface 130 of the groove have a circular cross-section. Furthermore, the illuminating device 118 is provided at a top side with a slit 132 which is cut open and formed along the moving axis of the pad. When the pad 10 is located at the inspecting position, the light is introduced into the cameras 114, 116 through the slit 132.

Elongate light emitting devices 134 for use in the monochrome linescan camera are installed at positions of the illuminating device corresponding to the monochrome linescan camera 114. The light emitting devices 134 for use in the monochrome camera are fixed at both sides of and positions close to the slit 132, respectively, so that the light can be incident onto the pad as perpendicularly as possible. Moreover, it is preferred that no shadows of the grooves of the pad be produced by the illuminating device. To this end, it is necessary to arrange the light emitting devices exactly perpendicular to the circumferential grooves of the pad. As shown in the figures, it is preferred that each of the light emitting devices 134 be a narrow, planar, elongate array of the LED elements.

Similarly, light emitting devices 136 for use in the color linescan camera are installed at positions of the illuminating device corresponding to the color linescan camera 116. As shown in the figures, it is preferred that each of the color light emitting devices be an arc shape which can cover an entire reflecting surface of the illuminating device and be an array of the LED elements which are long in the radial direction of the pad. It is preferred that white LED elements be employed for the LED elements so as to represent original colors of the pad as accurately as possible. Although it is not specifically illustrated, it is preferred that a transparent or semitransparent diffuser plate for scattering the light is installed in the front of the color light emitting elements. Of course, the diffuser plate is not installed on a light path which is extended from the pad to the color linescan camera.

Preferably, a length of each light emitting elements 134, 136 be longer than the pitch by which the pad 10 is shifted for its inspection. That is, it is preferred that the pitch be shorter than a length of a subject to be imaged at one time by the camera as well as a length of the light emitting element.

Referring again to FIG. 4, the apparatus 100 for inspecting the defects on the pad includes a central control unit 140. The central control unit 140 can be constructed using a conventional personal computer (PC). The PC used as the central control unit 140 includes a processor 142, a memory 144, and a storage device 146 (an auxiliary memory). Various kinds of processors such as a commonly used Intel's Pentium Processor may be used as the processor 142.

The central control unit 140 includes first and second frame grabbers 148, 150. The first grabber 148 is connected to the color linescan camera 116 and the second frame grabber 150 is connected to the monochrome linescan camera 114. Each of the frame grabbers 148, 150 captures the electrical signal transmitted from each of the cameras 114, 116 and converts the signal into corresponding digital signal. Each of the frame grabbers 148, 150 is installed in the form of a card inserted into a slot of the PC. These frame grabbers 148, 150 are known as a product called PC-Linescan which is available from Coreco, Inc. in Quebec, Canada (it is known in the name of Coreco Imaging even in Korea and its own internet website is www.imaging.com.)

The central control unit 140 includes a digital input/output board 152. The digital input/output board 152 transmits driving signals for the vacuum attachment device for driving the vacuum attachment fixture provided on the turntable and driving signals for various kinds of relays and solenoids which are not specifically illustrated, and simultaneously receives signals transmitted from a sensor such as a limit sensor and input signals from various buttons. More specifically, the digital input/output board is composed of a plurality of relays (4 to 16 relays) and a signal input device, and inspects state of external switches or on-off switches of external devices. Further, the digital input/output board performs functions of inputting signals from start, stop and emergency stop buttons, a home sensor of the turntable, and a limit sensor and home sensor of the linear moving device, and functions of switches of the solenoids for supplying vacuum and compressed air.

The central control unit 140 includes a two-axis motion control unit 154 which controls device drivers for controlling the drive motors provided in the turntable 110 and the linear moving device 112.

The display device 120 and input device 122 are connected to the central control unit 140. In the meantime, the apparatus 100 for inspecting the defects on the pad further comprises an encoder distributor 156 which is connected to an encoder 128 provided in the turntable 110 and to the respective frame grabbers 148, 150. The encoder distributor 156 transmits control signals to the frame grabbers 148, 150 so that the frame grabbers 148, 150 can capture the electrical signals from the linescan cameras in synchronism with the rotation of the turntable 110. To this end, the encoder distributor divides each of the pulses generated from the drive motors into two pulses, which are then transmitted to a capture board for use in the color and monochrome linescan cameras.

The defect inspection apparatus 100 comprises a motor driver 158 for driving the rotary drive motor 126 of the turntable 110 and a motor driver 160 for supplying electric power to the drive motor 113 of the linear moving device 120. The driver 158 for the rotary motor 126 of the turntable 110 also supplies the rotary motor with the electric power for driving the motor, and may control the motor based on signals from the encoder.

Various kinds of application programs and an operating system (OS) are stored into the storage device. In particular, a program for processing the acquired image data is stored in the device. The program is used to determine whether there are any defects on the pad by processing the image data acquired by the driving of the processor according to a process to be described later. By executing the program as such, a data processing unit can be formed in the central control unit 140. Although it has been described in the present embodiment that the PC is implemented into the central control unit 140, the present invention is not limited thereto. It can be understood by those skilled in the art that the central control unit can also be implemented by constructing hardware units such as the image data acquisition unit, image data processing unit and 2-axis motion control unit of the central control unit 140 and connecting them with one another.

Figure 7:
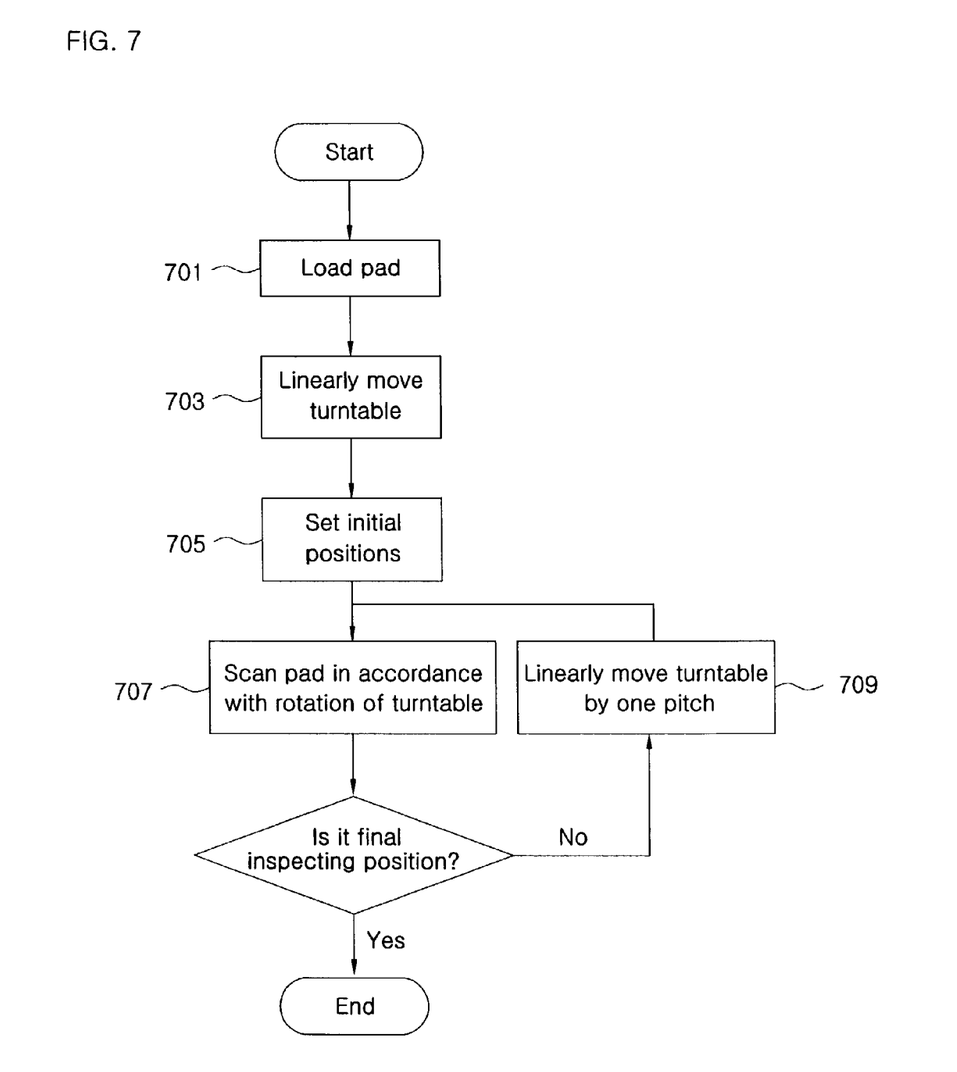
FIG. 7 is a flowchart illustrating a scanning process of inspecting the defect on the polishing pad.

Hereinafter, a process of detecting defects on the pad 10 will be described. Referring to FIGS. 2, 3 and 7, the linear moving device 112 is driven to move the turntable 110 to the loading position of the pad. The pad 10 to be inspected is loaded onto the turntable 110 (step 701). The linear moving device 112 is driven again to move the pad 10 to the inspecting position (step 703).

First, a monochrome image of the pad is acquired using a monochrome linescan camera 114. When the monochrome image of the pad is acquired, for example, an image of a section of the pad having a width corresponding to ⅛ of the radius R of the pad 10 (R/8; pitch) is acquired per revolution (the present invention is not limited to division into eight sections having the width of R/8). To this end, when an initial position of the pad is set (step 705), a position spaced apart by a distance of R/16 from an outermost edge of the pad 10 should be aligned with the center of the monochrome linescan camera 114. The line LEDs of the illuminating device 118 are supplied with electric power to illuminate a surface of the pad. In such a way, preparations for scanning the surface of the pad are completely made.

Thereafter, the turntable 110 is rotated. The monochrome linescan camera 114 performs the scanning of the pad for acquiring the monochrome image of the pad (step 707). Electrical signals corresponding to the image are transmitted to the second frame grabber 150 and then captured. Subsequently, they are converted into digital signals, and the converted digital signals are stored as one frame in a memory or storage device. At this time, the rotation of the turntable 110 and the data acquisition of the second frame grabber 150 are synchronized with each other.

After one data frame (sector) has been obtained, the linear moving device 112 linearly shifts the turntable 110 by one pitch (R/8) (step 709). After the shift of the turntable, the turntable 110 is rotated again so that the pad is scanned to acquire an image and then obtain the next data frame. Thus, the scanning of the entire surface 11 of the pad can be completed by repeating the scanning operations through the linear movement and the rotation of the turntable in such a manner. Even after respective shifts, the turntable 110 is rotated at different speeds for maintaining the substantially same or similar scanning rate. That is, the rotational speed (angular speed) becomes slower when the edge of the pad is scanned, whereas it becomes relatively faster when a central section of the pad is scanned.

Next, the scanning is performed by using a color linescan camera 116 to acquire a color image and thence data thereon. The process of performing the scanning of the pad by using the color linescan camera 116 is generally identical with that performed in the scanning of the pad by the monochrome line scanning camera 114. When the scanning is performed by using the color linescan camera 116, the width scanned at one time can become wider. For example, each one of two sections obtained by equally dividing the radius R by 2, i.e. each section having the width of R/2, is scanned at one time.

The image data obtained in such a way are analyzed to detect defects through gray scale processing, intensity value processing, saturation (also referred to as "chroma") value processing, and hue value processing which will be described later. The basic method of determining the kinds of respective defects is the same method as already described. When the inspection of the defects is completed, the results of the inspection are displayed on the display device.

Figure 8A:
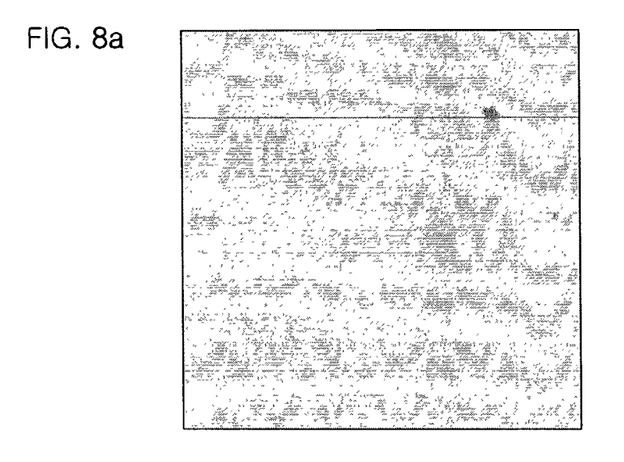
FIGS. 8 and 9 are views illustrating data processing results of particle detection for easy and visual understanding.
Figure 8B:
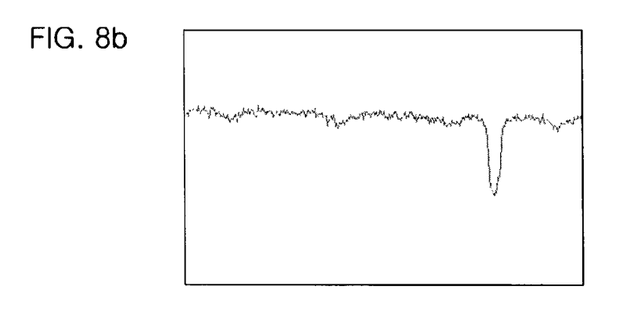

Hereinafter, a method of detecting defects by acquiring and processing the image data will be described. First, a process of detecting particles based on the gray scale (also referred to as "gray level" and indicating the brightness of light) will be explained. FIG. 8a shows an image with the particles. FIG. 8b shows gray scale values along a red line indicated in FIG. 8a based on the frame data on the image. As can be understood from FIG. 8a, the groove portions and particle portions are shown dark and their gray scales are small. Therefore, if a particular gray scale is defined as a threshold and the portions having gray scales lower than the threshold are considered as particle defects, there is a risk that the groove portions are also determined as the defects. Accordingly, since it is difficult to discriminate between the grooves and the particles, it is preferable to eliminate groove components from the final gray scale.

As can be seen from FIG. 8b, the surface of the pad has a coarse gray scale due to pores thereon. At this time, since it is difficult to clearly discriminate the particles from the pores, the effects of the pores should be eliminated. To this end, an average value of the gray scales for pixels around each specific pixel should be obtained. As can be seen from FIG. 8c showing the average value, the effects of the pores are eliminated and groove components are clearly shown.

The average value is obtained, for example, by averaging gray scale data acquired while rotating the turntable by a predetermined circumferential length or angle from any one dot on a radial line of the pad which is scanned by the monochrome line-scan camera. More specifically, the sections of the pad having the width corresponding to ⅛ of the radius of the pad are scanned by the monochrome line-scan camera. The radial unit width that is scanned at one time is composed of 2048 dots. Namely, this means that a line traversing the unit width is composed of 2048 dots. When such 512 radial lines are scanned while rotating the pad, data on the 512 lines construct one sector (also referred to as "frame"; The term "sector" used herein means a group of lines to be processed at one time. The term "frame" is a term used in the field of the frame grabber. In general, the frame is a unit by which an area scan camera performs the scanning at one time. Although an embodiment of the present invention utilizes the line-scan camera, processing of a plurality of scanned lines as a group is advantageous over separate processing of each scanned line in view of a processing rate and operation. Therefore, even though the embodiment of the present invention performs the scanning on a line basis, for example, 512 lines are grouped into a sector and then processed on a sector basis. Herein, the sector is referred to as the frame). If the radius of the pad is equally divided into 8 segments, data on an outermost edge section of the pad during one revolution can be composed of 51 sectors. As for data on an innermost central section of the pad, data acquired during one revolution can be composed of 26 sectors.

The 512 lines in one section of the pad are divided again into four subsections and an average value for each subsection is obtained. That is, gray scale values for respective 2048 dots obtained from 128 lines are averaged to obtain the average value. Of course, the present invention is not limited to the aforementioned exemplary method of obtaining the average value. The aforementioned method of obtaining the average value is for illustrative purposes only.

Figure 8C:
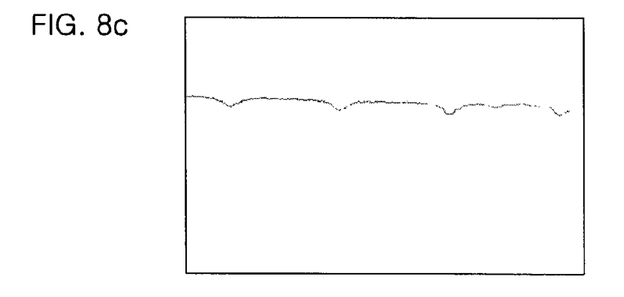
Figure 8D:
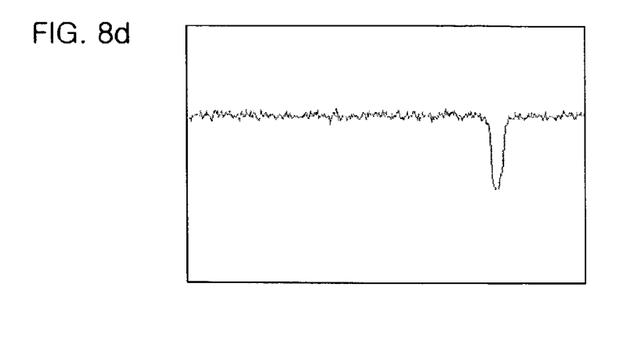

Thereafter, the average value shown in FIG. 8c is subtracted from the gray scale of the pixel shown in FIG. 8b. Then, an averaged gray scale with the groove components removed therefrom is obtained as shown in FIG. 8d. In FIG. 8d, a position where the gray scale is smaller than a predetermined value is detected as a defect.

Figure 9A:
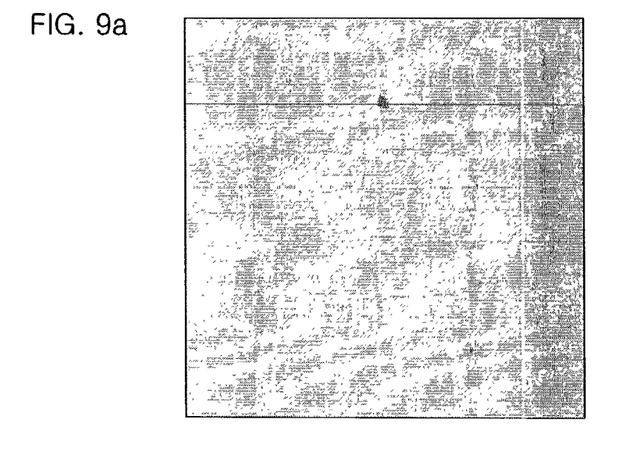
Figure 9B:
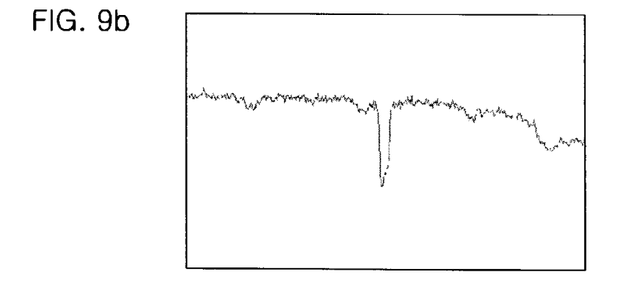

Since a camera lens has a spherical surface, the amount of light passing though the lens becomes smaller while being closer to an edge of the lens. Therefore, under the same illumination condition, a central portion of the lens is bright, whereas it becomes darker while being closer to the edge of the lens. Accordingly, it is difficult to determine the particles through edge portions of the lens. In order to solve the problem, there has been proposed a method of utilizing a lens of large aperture. However, the problem cannot be completely solved only by the lens, and consequently, a gray scale shown in FIG. 9b is obtained. FIG. 9b shows the gray scale along a horizontal line shown in FIG. 9a. It can be seen from the figure that the luminous intensity is gradually lowered toward a right end and is lower than the gray scale of the particle nearly at the right end. Thus, if the particle is determined only based on a predetermined threshold, the right end is also determined as the particle.

Figure 9C:
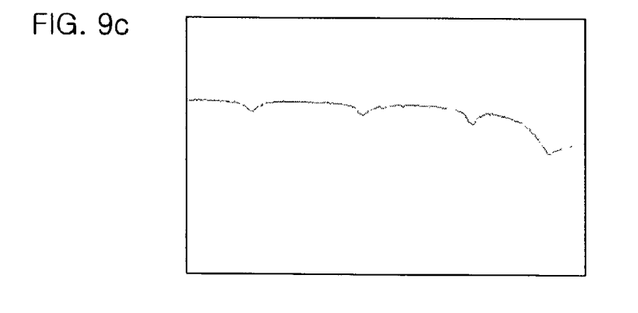
Figure 9D:
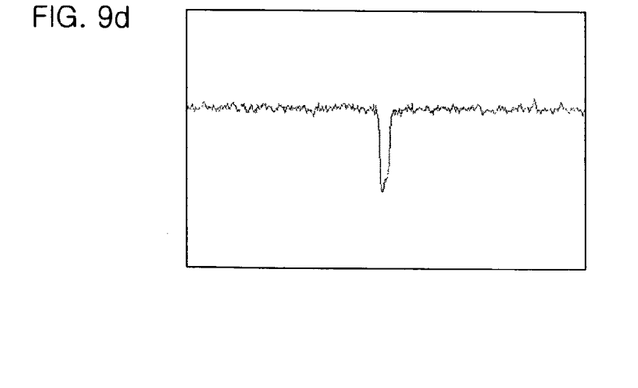

In order to solve such a problem, an averaged gray scale shown in FIG. 9c is obtained in the same way as described above. When the averaged gray scale shown in FIG. 9c is subtracted from the gray scale of the pixel shown in FIG. 9b, a variation in the luminous intensity is removed, and thus, only particle signals remain. As a result, the effect of the luminous intensity is eliminated, and thus, the particles can be easily and accurately detected.

Detection of a defect such as a spot of which signal contrast is weak is achieved by using the color line-scan camera 116. Signals of an image captured by the color linescan camera 116 are separated into values of RGB and HSI (referred to as "three components of light"; abbreviation of "Hue, Saturation, and Intensity") and the separated values are recombined to amplify the image contrast. By using the values of RGB and HSI, the defect is detected based on the aforementioned characteristics of the spot.

In a case where a defect is difficult to be detected by using the monochrome gray scale, it is possible to make new standards in which the defect is experimentally detected using scan data acquired by the color line-scan camera. First, the RGB values of the image data acquired through the scanning by the color line-scan camera 116 are converted into the values of HSI which is the three components of light. By combining a total of 6 signals obtained in such a way, it should be experimentally found out which signal of the 6 signals has a largest difference in the respective values between the defect and a normal surface of the pad and what is a threshold for determining the defect. Thus, as for a specific kind of defect, the defect can be promptly determined based on a signal value which is preferred to be compared among the 6 signals. This method can be applied to a case where a new kind of defect is found out. The value to be compared can be defined, for example, as a formula, i.e. Level=I·$f_i$−S·$f_s$, where $f_i$ is a coefficient of the intensity and $f_s$ is a coefficient of the saturation. A portion in which there is a predetermined difference between the defined level value and the level value of the normal surface of the pad is determined as the defect.

Meanwhile, the central control unit 140 detects the defects through such a process and then can perform statistical processing by images, sizes and kinds of the defects. With the statistical processing, a user can understand a trend of the polishing pad for a short or long period of time and hence any correlations with processes and a yield.

The defect inspecting apparatus 100 according to the present invention can be further provided with a camera capable of imaging a moving picture. In this case, there is convenience in that defects detected by the defect inspecting apparatus can be confirmed through the moving picture.

Although it has been described that the scanning is performed while rotating the turntable in the previous embodiment, the scanning may be alternatively performed by using an X-Y table.

According to the constitution of the present invention, there are advantages in that the defects on the pad are inspected so that a failure in processes which may be caused by the pad can be avoided in advance and a solution to future improvement of the processes can be obtained by discovering causes of the defects which have been already produced. Furthermore, according to the present invention, the statistical processing is performed by images, sizes and kinds of the defects after the defects are detected, so that the user can understand the trend of the polishing pad for a short or long period of time and hence any correlations with the processes and the yield.

Since the turntable is utilized, the signal effects of the groove portions on the pad can be minimized. The constitution of the defect inspecting apparatus is simplified by employing the turntable structure as a structure for moving the pad. The turntable structure requires only a relatively small space for shifting the pad. By rotating the pad on the turntable, making the illumination direction and the rotation direction be perpendicular to each other, and arranging the line CCD of the camera in a direction perpendicular to the pad, the signal contrast between the groove portions and the surface of the pad can be minimized. The camera with the color line CCD installed therein is used so that intrinsic defects such as a spot of which the contrast is not clear can be certainly detected.

What is claimed is:

1. An apparatus for detecting or inspecting defects on a pad for use in performing chemical mechanical polishing of a wafer, comprising:
    a pad driving device for loading the pad thereon and moving the pad;
    a camera installed to face the pad for converting an image of the pad into an electrical signal and outputting the converted electrical signal;
    a digital image data acquisition device for converting the electrical signal transmitted from the camera into a digital signal; and
    an image data processing unit for processing the image data and detecting the defects on the pad, wherein the image data processing unit calculates one or more of quantitative characteristic values of light based on the image data on any one of the points which are acquired from the image data acquisition device, and determines a location on the pad, where a difference between a level value obtained by combining one or more of the acquired quantitative characteristic values and a level value obtained from a normal surface of the pad is greater than a predetermined value, as a defect.

2. The apparatus as claimed in claim 1, wherein the camera is a linescan camera including a monochrome or color line CCD extending in a radial direction of the pad.

3. The apparatus as claimed in claim 2, wherein the pad driving device includes a turntable for causing the pad to rotate about the substantial center thereof, and the line CCD of the linescan camera is disposed such that a longitudinal direction thereof is coincident with the radial direction of the pad.

4. The apparatus as claimed in claim 3, further comprising an illuminating device installed between the camera and the pad, wherein the illuminating device includes a supporting body in which a slit extending in the radial direction of the pad is included, and a light emitting device which extends along the slit and is installed around the slit to face the pad.

5. The apparatus as claimed in claim 4, wherein the supporting body is provided around the slit with a groove of which cross-section is semicircular, and the light emitting device includes an elongate circular white light source LED array which can cover at least a portion of a surface of the groove in its longitudinal direction.

6. The apparatus as claimed in claim 4, wherein the supporting body is provided around the slit with a groove of which cross-section is semicircular, and the light emitting device includes an elongate LED array which is installed around the slit along at least a portion of a surface of the groove and is substantially narrow.

7. The apparatus as claimed in claim 1, further comprising an illuminating device facing a surface of the pad.

8. The apparatus as claimed in claim 1, wherein when processing data on any one specific point on the pad, the image data processing unit calculates an average of the level values of points adjacent to the specific point and subtracts the average level value from the level value of the specific point.

9. The apparatus as claimed in claim 8, wherein the adjacent points selected for calculating the average value by the image data processing unit are located on a line extending from the specific point along a shifting direction of the pad.

10. The apparatus as claimed in claim 1, wherein the quantitative characteristic values of the light acquired from the image data processed in the image data processing unit are HSI values.

11. The apparatus as claimed in claim 1, wherein the pad driving device includes a turntable for causing the pad to rotate about the substantial center thereof, and a pulse signal corresponding to a predetermined angle of rotation of the turntable is synchronized with a trigger signal of the image data acquisition device.

12. The apparatus as claimed in claim 11, wherein the turntable includes a rotary stepping motor, and the pulse signal corresponding to the predetermined angle of rotation of the turntable is a step pulse signal of the stepping motor.

13. The apparatus as claimed in claim 11, wherein the turntable includes a rotary encoder and an encoder distributor connected to the rotary encoder, and the encoder distributor is connected to the image data acquisition device to transmit the pulse signal to the image data acquisition device.

14. The apparatus as claimed in claim 1, wherein the data processing unit includes a processor and a storage device, and a program for driving the processor is stored in the storage device.

15. A method for detecting or inspecting defects on a polishing pad for use in performing chemical mechanical polishing of a wafer, comprising the steps of:
rotating the polishing pad about the center thereof;
acquiring an image of a top surface of the polishing pad along a line extending in a radial direction thereof;
converting the image into an electrical signal;
converting the electrical signal into digital image data; and
processing the digital image data, wherein the step of processing the image data comprises the steps of calculating one or more of quantitative characteristic values of light based on the image data on any one of the points which are acquired from the image data acquisition device, and determining a location on the pad, where a difference between a level value obtained by combining one or more of the acquired quantitative characteristic values and a level value obtained from a normal surface of the pad is greater than a predetermined value, as a defect.

16. The method as claimed in claim 15, wherein in order to process data on any one specific point on the pad, the step of processing the image data comprises the steps of calculating an average of the level values of points adjacent to the specific point and subtracting the average level value from the level value of the specific point.

17. The method as claimed in claim 16, wherein the adjacent points selected for calculating the average values in the step of processing the image data are located on a line extending from the specific point along a shifting direction of the pad.

18. The method as claimed in claim 15, wherein the quantitative characteristic values of the light acquired from the image data processed in the step of processing the image data are HSI values.

19. The method as claimed in claim 18, wherein the level value L is calculated in accordance with the following equation:

$$L = I \cdot f_i - S \cdot f_s,$$

where I is an intensity value, $f_i$ is a coefficient of the intensity, S is a saturation value, and $f_s$ is a coefficient of the saturation.

20. An apparatus for detecting or inspecting defects on a pad, comprising:
a pad driving device for loading the pad thereon and moving the pad;
a camera installed to face the pad for converting an image of the pad into an electrical signal and outputting the converted electrical signal;
a digital image data acquisition device for converting the electrical signal transmitted from the camera into a digital signal; and
an image data processing unit for processing the image data and detecting the defects on the pad, wherein the image data processing unit includes a processor and a computer-readable recording medium into which a program executed by the processor is recorded, the program comprising instructions for causing the processor to execute the steps of:
calculating one or more of quantitative characteristic values of light based on the image data on any one of points which are acquired from the image data acquisition device; and
calculating a difference between a level value obtained by combining one or more of the acquired quantitative characteristic values and a level value obtained from a normal surface of the pad and confirming whether or not the difference is greater than a predetermined value.

* * * * *